United States Patent [19]

Hudson et al.

[11] Patent Number: 5,125,034
[45] Date of Patent: Jun. 23, 1992

[54] METHOD AND APPARATUS FOR ANALYZING FABRIC CONDITIONS

[75] Inventors: Rick L. Hudson, China Grove, N.C.; Michael G. Belanger, Oak Park, Ill.

[73] Assignee: Compax Corp., Lexington, N.C.

[21] Appl. No.: 635,668

[22] Filed: Dec. 27, 1990

[51] Int. Cl.⁵ .............................................. G06K 9/00
[52] U.S. Cl. .......................................... 382/1; 382/8; 26/51.5; 139/1 D; 356/238; 356/241; 364/470
[58] Field of Search ............... 356/238, 242; 139/1 D; 26/51.5, 70; 382/1, 8; 364/470; 73/159; 377/3, 10

[56] References Cited

U.S. PATENT DOCUMENTS

| | | | |
|---|---|---|---|
| 3,517,204 | 6/1970 | Mahlo et al. | 356/238 |
| 4,248,533 | 2/1981 | Shimada | 356/238 |
| 4,255,050 | 3/1981 | Beckstein et al. | 26/51.5 |
| 4,414,476 | 11/1983 | Maddox et al. | 26/515 |
| 4,586,372 | 5/1986 | Massen | 73/159 |
| 4,812,140 | 3/1989 | Russell et al. | 8/493 |
| 4,890,924 | 1/1990 | Beckstein | 26/51.5 |
| 4,953,400 | 9/1990 | Bossuyt | 356/238 |
| 4,954,962 | 9/1990 | Evans, Jr. et al. | 364/513 |
| 4,961,149 | 10/1990 | Schneider et al. | 358/107 |

FOREIGN PATENT DOCUMENTS 2487867 2/1982 France ............... 139/1 C

*Primary Examiner*—Leo H. Boudreau
*Assistant Examiner*—Barry Stellrecht
*Attorney, Agent, or Firm*—Schweitzer Cornman & Gross

[57] ABSTRACT

A system for analyzing fabrics, knitted or woven, particularly to perform in-process analysis of stitch count or yarn count. A camera positioned over the fabric is exposed by means of a high speed strobe to form a freeze-frame image, which is digitized and stored for computer processing. An early processing step involves scanning the image along a large number of angularly displaced scanning axes, to determine the construction line of the fabric, which may be skewed relative to the imaging camera. The image is thereafter scanned along lines parallel to (and/or at right angles to) the construction line. A more precise and useful analysis is made possible by this technique. Color insensitivity is achieved without the use of expensive infra-red strobe devices, by using a common xenon strobe and a filter to exclude wave lengths below the near-infra-red range.

8 Claims, 6 Drawing Sheets

METHOD AND APPARATUS FOR ANALYZING FABRIC CONDITIONS

BACKGROUND AND SUMMARY OF THE INVENTION

In the processing of fabrics, both knitted and woven, an important characteristic of the fabric is the number of yarns or stitches per unit of length, particularly in the length direction. These characteristics can change significantly during fabric processing and thus can and do reflect the influence of the processing.

Because of the importance of monitoring fabric characteristics during processing, numerous attempts have been made to evaluate fabric characteristics on a real time basis, without stopping or otherwise interfering with the processing operations.

One known system for monitoring fabric condition involves the use of an optical device capable of counting the number of yarns or stitch courses passing by an optical sensing element during fabric processing. This device is utilized in combination with a measuring wheel, maintained in contact with the fabric, to determine the linear rate of fabric passage. By combining the linear rate of fabric passage with the count of the stitch courses, a relative measure of stitch courses per linear unit can be derived.

Another known system for measuring fabric characteristics involves the use of an imaging camera arranged to take and store an image of the fabric, and to electronically analyze the stored image to ascertain fabric characteristics. The last described system has advantages over that first described, in that it does not require physical contact with the fabric. Nevertheless, the latter system has important shortcomings, in that it is quite costly and has important limitations in relation to the information derived therefrom.

In accordance with the present invention, a novel and improved system is provided for analyzing fabric characteristics on a real time, in-process basis, in a manner to provide a more accurate and more useful measurement of fabric characteristics than has been available using prior art systems. In this respect, fabrics being handled on processing lines, both woven and knitted, but particularly knitted fabrics, can become considerably skewed in the course of processing such that, for example, their stitch courses, in the case of knitted fabrics, or warp yarns, in the case of woven fabrics, are not perpendicular to the longitudinal axis of the fabric. Additionally, even if the yarns or stitch lines are symmetrical with respect to the longitudinal axis, the cross lines of the fabric may become bowed, with the center portion of the fabric either leading or lagging the edge portions. The method and system of the present invention enable these skewed conditions to be both detected and evaluated. This not only enables in-process correcting adjustments to be made on a real time basis, but also enables greater accuracy to be realized in the determination of the number of stitches per unit of length, because such determination takes into account the existing skew condition of the fabric.

Pursuant to the present invention, a digitized freeze-frame image of the fabric is taken and stored, and then analyzed electronically. As a particular feature of novelty, the method and system of the present invention involves initially examining the freeze-frame image along a series of axes, each slightly angularly displaced from the other. By comparison of these several analyses, it is possible to identify lines of stitches in the fabric (hereinafter referred to generically as construction lines of the fabric) regardless of angularity thereof. Having thus identified the orientation of the fabric construction line, in relation to the orientation of the digitized image, the image is then electronically analyzed along lines parallel with and/or at right angles to the identified construction line. Out of this analysis is derived not only a highly accurate stitch count, but also a quantitative measure of the skew angle of the fabric construction line.

By using a plurality of imaging cameras located across the width of a moving fabric web, or a traversing camera arrangement for taking and processing successive images across the width of the fabric, it is also possible to detect and quantify bowing of the fabric across its width.

In known systems for obtaining digitized, freeze-frame images of a fabric for analyzing construction characteristics, it is known to utilize infrared light sources, as a means of minimizing any sensitivity of the imaging apparatus to changes in colors of the fabric passing underneath. While this arrangement is quite effective, it is somewhat costly. In accordance with the present invention, a conventional xenon strobe unit can be utilized to provide light energization for the imaging camera. However, the imaging source is filtered to substantially eliminate light in the visible range, so that the remaining light, capable of energizing the imaging camera, is the near infrared and infrared ranges. The arrangement efficiently achieves insensitivity to color changes in the fabric, but with greater simplicity and at a significantly lower cost than using conventional infrared technology.

Overall, the system of the invention enables a higher degree of precision to be achieved in the determination of fabric characteristics, enables skew conditions to be detected and quantified, and at the same time may be provided at a significantly lower cost than the known systems currently available.

For a more complete understanding of the above and other features and advantages of the invention, reference should be made to the following detailed description of a preferred embodiment of the invention, and to the accompanying drawings.

DESCRIPTION OF A PREFERRED EMBODIMENT OF THE INVENTION

Figure 1:
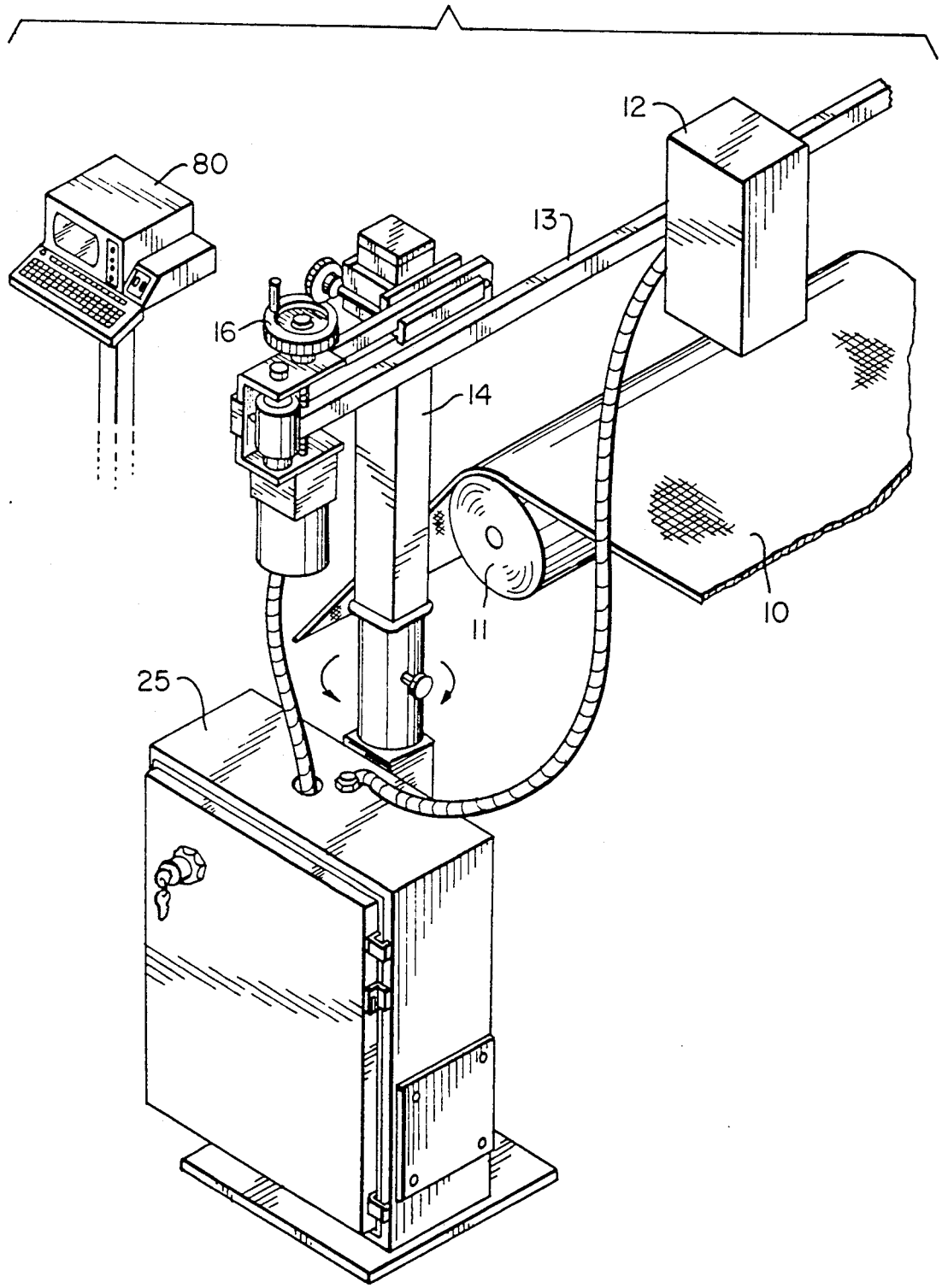
FIG. 1 is a simplified schematic representation of a typical, single station system according to the invention for real time monitoring of fabric characteristics during processing.

Referring now to the drawings, and initially to FIG. 1 thereof, the reference numeral 10 designates an in-process fabric, which is moving from left to right in FIG. 1 and passing over a guide roll 11. An imaging unit 12, to be further described, is mounted directly above the fabric 10. In a typical system according to the invention, the imaging unit may be mounted on a horizontal arm 13 adjustably positioned on a mounting post 14 at the side of the processing line. The imaging unit 12 is adjustable laterally along the mounting arm 13, and the mounting arm 13 is adjustable vertical along the post 14. Motor means 15 and/or manual elements 16 may be provided for adjusting purposes. The particular arrangement for mounting of the imaging unit does not form a part of the invention.

Figure 2:
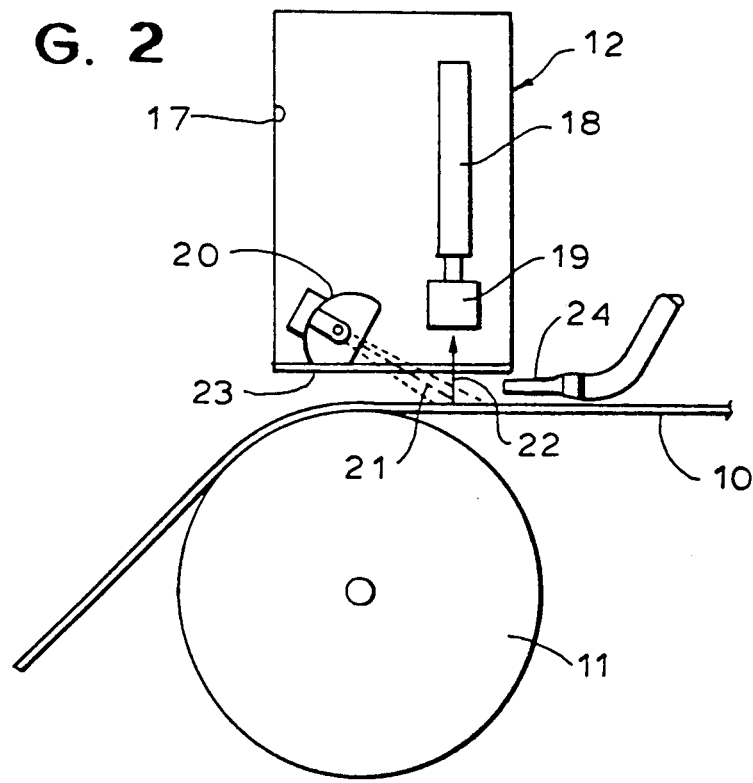
FIG. 2 is an enlarged, simplified representation of a portion of the system of FIG. 1, illustrating the arrangement of the imaging system relative to the fabric.

With reference to FIG. 2, the imaging unit 12 advantageously includes a suitable housing or enclosure 17. Internally of the enclosure, there is mounted an imaging camera 18, of a type suitable for taking a digitized image of a predetermined sample area of the fabric 10 passing underneath. A suitable and desirable camera for the purpose is a Sony XC-77 CCD imaging camera. This camera has an image resolution of 752×480 8-bit pixels, each providing 0-255 intensity recognition.

To particular advantage, the imaging camera 18 is fitted with an Auto-Iris variable aperture control 19, as for example made available commercially by Computar. This enables the camera aperture to be enlarged or constricted, as necessary, for optimum imaging taking into account variations in fabric coloration, environmental influences, etc.

A strobe light 20 is mounted within the housing 17 and is arranged with its principal axis 21 disposed at an angle of about 45° or less to the plane of the fabric to being imaged. The strobe is located to one side of the imaging axis 22 of the camera 18, preferably aligned with the principal direction of stitch counting and preferably on the upstream side of the camera with respect to the direction of fabric movement. The strobe is arranged to momentarily illuminate an area of the fabric aligned with the imaging axis in such a way that the slightly protruding elements of the stitches are highlighted by the angled strobe light.

In order to minimize variations in imaging response as a function of fabric color variations, it is known to utilize infra-red strobe devices. Such devices are, however, quite costly. The system of the invention advantageously utilizes a common, relatively inexpensive xenon strobe light, in conjunction with a filter plate 23 that substantially screens out light of wave lengths in the visible range. Preferably, the filter plate 23 screens out wave lengths below about 830 nanometers, leaving light bands in the near infra-red bands to pass through to the imaging camera.

In the illustrated arrangement, the filter plate 23 serves as the entire bottom enclosure of the housing 17, which simplifies the construction of the housing.

To ensure that the region of the fabric being illuminated and imaged is free of dust, debris, steam, etc., it is advantageous to position an air nozzle 24 so as to direct a stream of clean air into the space between the fabric 10 and the filter plate 23. Best results are obtained by locating the nozzle 24 on the downstream side of the imaging device 12, to direct its air stream in an upstream direction. Any steam or the like being carried along with the fabric is thus prevented from passing under the imaging area.

In the system of the invention, the imaging camera 18 is associated with a processing system, physically represented by the reference numeral 25 in FIG. 1, which includes the various hardware and software components for processing and analyzing the data received from the imaging camera. In general, the hardware components are conventional computer (PC) system components. A significant add-on component for the purposes of the invention is the installation of a so-called Frame Grabber board, for example, the "4MEG VIDEO Model 10" board commercially marketed by Epix Inc., North-brook, Illinois. Such boards are available with 4 megabytes of image memory. The Frame Grabber board receives and stores as linear memory sequential 8 bit values received from the imaging camera. This image memory can then be accessed by the conventional PC/AT system for analysis under software direction according to the invention.

The software analysis of the fabric image sample, according to the teachings of the invention, is best explained with reference to the logic flow sheet diagrams of FIGS. 5-13.

A first step in the imaging process is the setting of a desired exposure level of the imaging camera 18, so that successive images are individually properly exposed and successive images are exposed with a controlled degree of uniformity. To this end, the taking of each freeze-frame imaging involves an initial step of making one or more strobe exposures of the fabric, analyzing the resulting image and determining whether the image exposure is at a desired level. If not, automatic incremental adjustment of the Auto-Iris element 19 is effected and a further exposure is taken. The process is repeated until the exposure level is within predetermined limits. In a normal sequence of operations, a single initial exposure is usually adequate to verify proper exposure. During start-up, however, or under difficult conditions, several exposures may be required.

Figure 4:
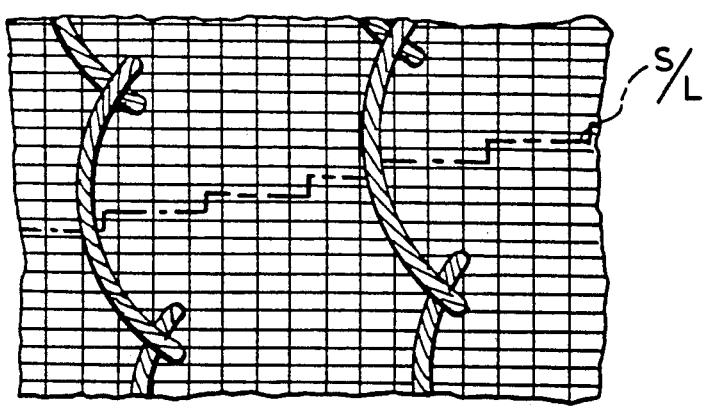
FIG. 4 is an enlarged view of an area of the image of FIG. 3.
Figure 6:
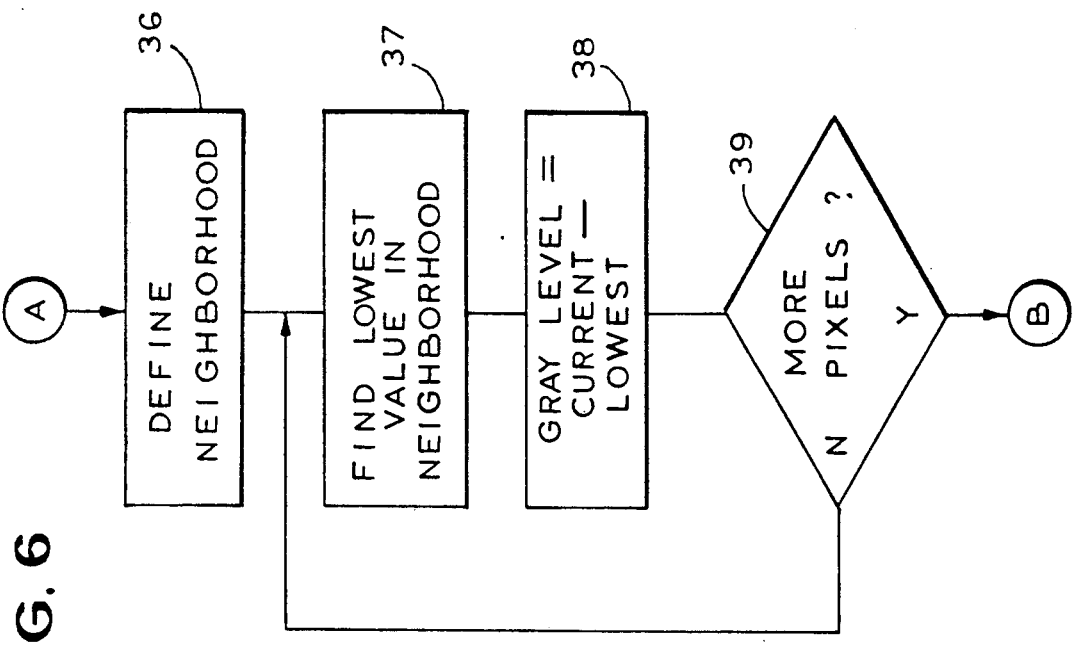
FIGS. 5–13 are successive views constituting a logic flow sheet for the control of the process of the invention.
Figure 5:
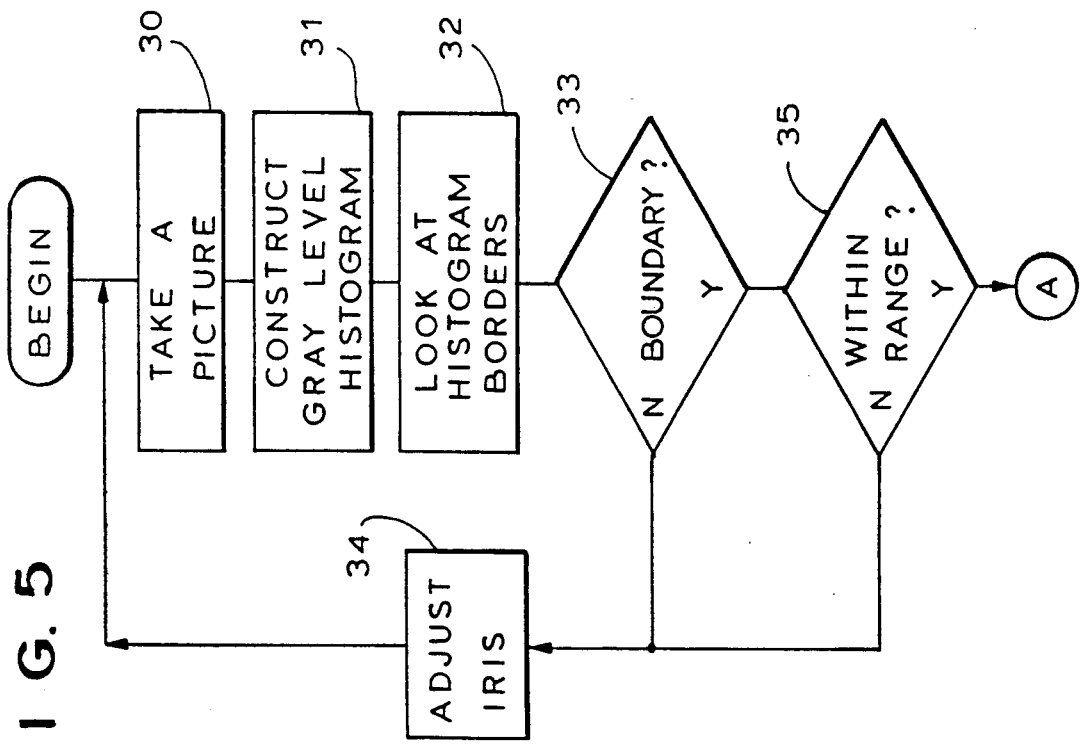

With reference to FIG. 5, the process commences with an initial imaging sample, reflected at logic point 30. This involves the triggering of the xenon strobe 20, the reception of the image by the camera 18, through the Auto-Iris element 19 and the transmittal of that image to the Frame-Grabber board. The image received by the camera 18 is digitized within the camera in individual pixels corresponding to small area segments of the image (see FIG. 4, for example). The individual pixels of the camera image are digitized according to the energy level of the pixel exposure, as an 8-bit (0-255) function. These pixel values are transmitted to the Frame-Grabber board and stored in individual memory cells on that board.

The Frame-Grabber board stores the individual pixel values according to the 8-bit value of pixel exposure. These pixel values are thereafter electronically scanned, and a gray level histogram is constructed by analysis of the gray levels (0-255) of the individual pixel values. This action is represented by the flow diagram logic point 31. The limits of the histogram are then analyzed, as reflected at logic point 32 of the flow diagram. If the histogram values are not within predetermined gross max/min values, the software logic at point 33 causes a gross adjustment to be made of the Auto-Iris (flow diagram logic point 34), and the process is repeated. When the histogram falls within the gross max/min limits, a further determination is made as to whether the histogram falls within the narrow limits of the desired adjustment (logic point 35). If not, an appropriate minor adjustment of the Auto-Iris is called for. When the exposure level is appropriate, the logic point 35 directs the process to the next stage.

During normal operation of the system, usually not more than a single preliminary image is required to properly adjust the Auto-Iris element 19. In some cases, the initial exposure will be appropriate, and the processing will proceed immediately.

When the image transmitted to the Frame Grabber board is determined to be at a proper exposure level, the processing and analysis of the image is initiated. The first step in the image processing is reflected in the logic flow diagram of FIG. 6. This involves processing of the individual image pixels to flatten the effects of varying light levels across the fabric and thereby facilitate the subsequent image analysis. For this purpose, each image pixel is analyzed in relation to a predetermined "neighborhood" of adjacent pixels. The specific selection of neighboring pixels may be different for different fabrics, although the pattern should be consistent for the same fabric. For many fabrics, the neighboring pixels may be selected along the "X" axis of the scan. The original definition of the neighborhood is a predetermined input to the software, and is represented by logic point 36 of the flow diagram. For each pixel evaluated, the software, as reflected by the logic point 37, examines the associated "neighborhood" and determines the lowest gray level value of the several pixels constituting the neighborhood. In the next logic point 38, the gray level for the pixel under evaluation is established by determining its actual value and subtracting therefrom the value of the lowest gray level value of the "neighborhood". This adjusted gray level value is stored in a separate memory cell, and the process is repeated via logic point 39 until the entire image has been evaluated and reconstructed. The reconstructed image contains gray level values adjusted downwardly in a manner that the difference between pixels is, percentagewise, greater than the initial values.

Figure 9:
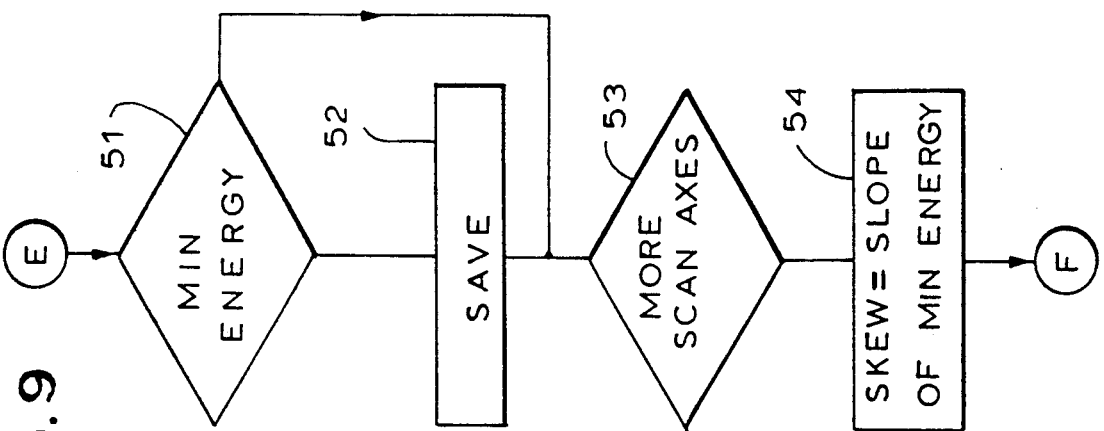
Figure 8:
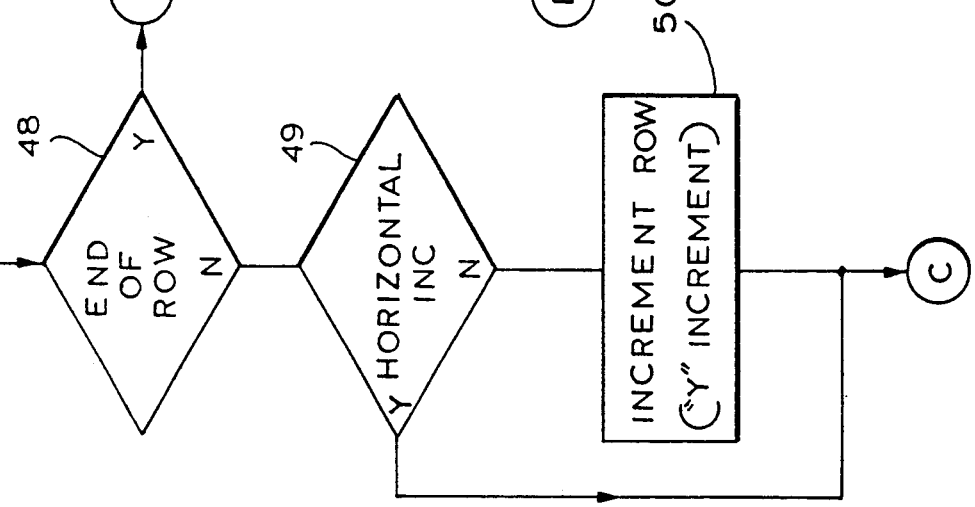
Figure 7:
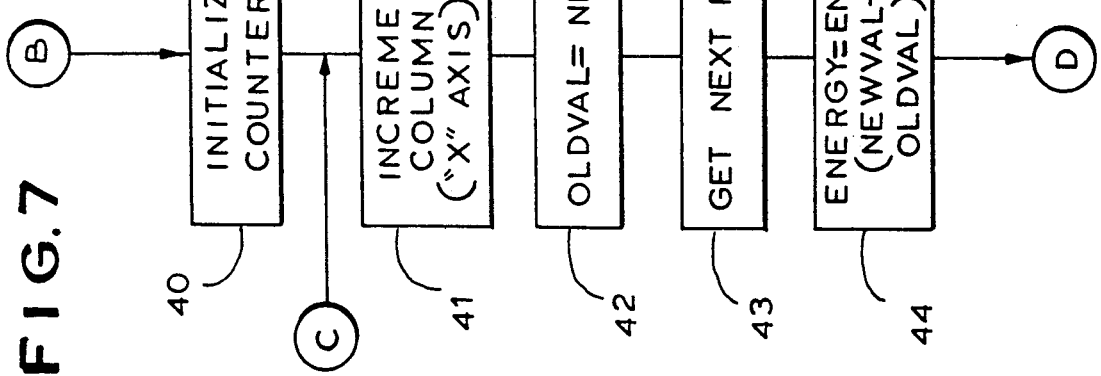

The next step of the image evaluation process, reflected in FIGS. 7-9 of the logic flow chart, is a feature of particular significance to the overall analysis routine. In this next analysis stage, the freeze-frame image, as modified in the manner just described, is examined along a series of axes, each displaced angularly slightly from the others. This analysis, to be described in further detail, enables a determination to be made of the orientation of the stitch lines (in a knitted fabric) or yarns (in a woven fabric) in relation to the orientation of the image itself. Desirably, the camera 18, and thus the sampling image, is oriented so that the "X" and "Y" axis of the image are aligned with the longitudinal axis of the moving fabric web, and a line at right angles thereto, respectively.

Figure 3:
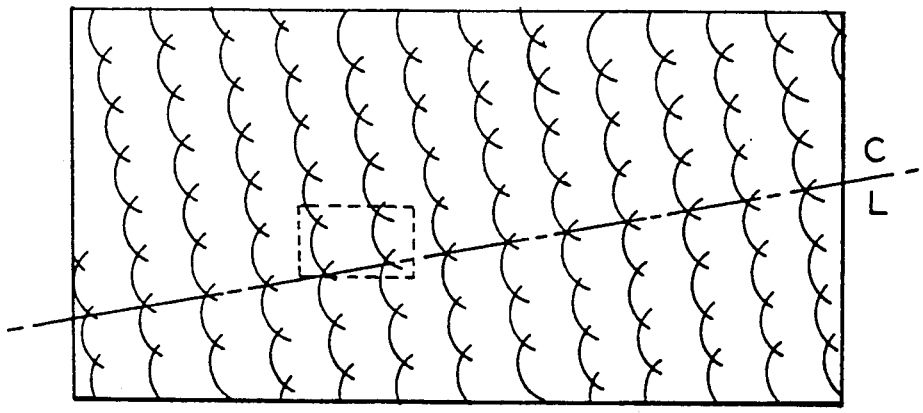
FIG. 3 is a representational illustration of an image of a sampling area of the fabric, showing the arrangement of stitches.

Particularly in the processing of knitted fabric, and to a lesser but still significant degree in the processing of woven fabrics, the stitch lines or lines may tend to become skewed relative to the axis of the web. For example, with a tubular knitted fabric, the fabric may tend to rotate slightly in a spiral fashion, causing the wales or longitudinal lines of stitching, to be skewed off at an angle relative to the longitudinal axis. This condition is reflected in FIG. 3 of the drawings, where the axis C/L of the stitch line is shown to be skewed at a substantial angle to the edges of the image (assumed to be properly oriented with respect to the fabric web). The fabric may also become bowed across its width, as where the center of the fabric tends to either lead or lag the fabric edges. Or the fabric may simply become skewed by one side edge tending to lead or lag the other. These are conditions that often can be corrected in processing, if identified.

In accordance with the procedure of the present invention, the first step in the analysis in a given freeze-frame image is to search for and identify the stitch lines or yarn lines of the fabric, hereinafter referred to generically as the construction line of the fabric. When the construction line is identified, and its skew angle quantified, corrective measures may be taken, either automatically or by operator intervention. Moreover, where the skew angle is greater than minimal, as may well be the case, a conventional count of stitch lines, taken either longitudinally or transversely along the usual orthogonal axes, can result in significant errors, in some cases because stitches that should be counted will be missed, or vice versa, and in other cases because the count will be in error by a function of the angle of skew.

Pursuant to the present invention, after identifying and quantifying the skew angle of the construction lines, stitch counting proceeds either along such lines or at right angles thereto, so that a highly accurate count of stitches per unit of length is realized.

The first step in the process of identifying the skew angle is to conduct a pixel-by-pixel analysis of the freeze-frame image, not along the usual X and Y axis, but in a programmed, stepwise combination of X and Y increments in a series of scans. For example, it may be appropriate to perform a series of, say, 26 scans each displaced about one degree from the other, covering an angular scope of about ±13° from an ideal axis.

With specific reference to FIGS. 7-9, the skew analysis is initiated by initializing counters as reflected by logic point 40. The initial scan angle is derived from a preprogrammed database, which sets the ratio of "X" increments to "Y" increment to define a particular scan axis, as for example the scan axis S/C represented in FIG. 4. At logic point 41, the scan is incremented along the "X" axis. The indicated scan value of the previously scanned pixel is saved for reference, as reflected by logic point 42, and the next indicated pixel is evaluated for its energy level (gray scale value) at logic point 43. A cumulative energy value for a given scan axis is derived at logic point 44 by adding to any previous cumulative energy value the difference between the energy value of the pixel just examined and the value of the previous pixel. A sharp difference in readings will add to the cumulative count a greater increment than if successively read pixels have similar values, as will be understood.

At logic point 48 (FIG. 8) the logic examines whether the pixel row, in the line of the selected scan axis, has ended. If not, the program proceeds to logic point 49 to determine whether the increment to the next pixel is an "X" increment. If not, a "Y" increment is carried out, as reflected at logic point 50, and the loop returns to logic point 41 (FIG. 7), to evaluate successive pixels along the chosen scan line.

When the end of all rows along a given scan line has been detected, the program branches to logic point 51 (FIG. 9) where the cumulative energy value derived at logic point 44 is evaluated by comparison with the previous lowest cumulative energy total. If the more recent total is lower than any previous total, that value and its scan axis is stored in memory, as reflected by logic point 52. Otherwise, the program bypasses the logic point 52. In either case, the program proceeds to evaluate, as reflected at logic point 53, whether there are additional angularly displaced scan axes to be evaluated. If so, the program loops back to logic point 40, reinitializing the counters, obtaining a new horizontal increment value to define the new scan axis angle, and proceeding to evaluate all pixels along the new scan axis.

When all of the predetermined scan axes have been evaluated, the memory segment controlled at logic point 52 will identify that scan axis in which there was the least amount of change in energy value from pixel to pixel along the entire length of the scan. This minimum value clearly indicates that the orientation of the axis along which that particular scanning operation took place coincides with the construction line or construction axis of the fabric. By contrast, if the scan extends along an axis that repeatedly crosses stitch lines and lines between stitches, there will be successive significant energy differentials and thus a relatively high accumulation of energy values. But where the pixel-to-pixel scan proceeds along a construction line, energy values of successive pixels will tend to be similar and the accumulation that is indicated at logic point 44 is relatively minimal. The end result of this initial analysis is represented by logic point 54 (FIG. 9).

Figure 11:
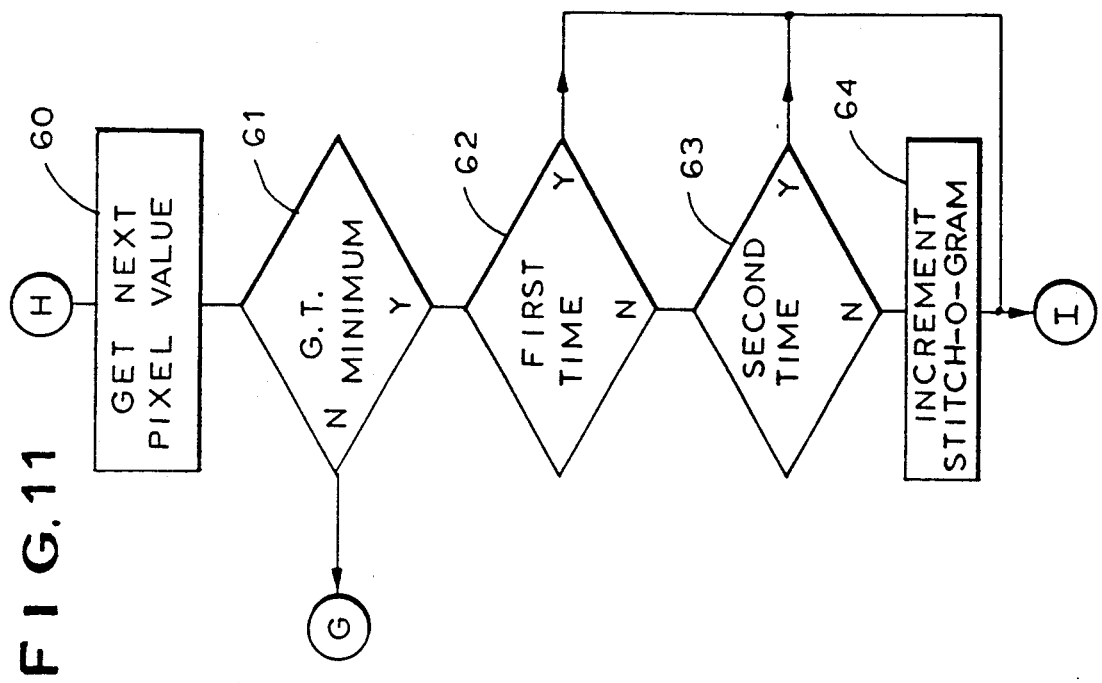

Having identified the skew angle of the construction line, the further analysis of the freeze-frame image proceeds along such axis, or in appropriate cases, at right angles thereto, or both. In the illustrated system, the primary objective is to obtain a count of stitches in the longitudinal direction, so the principal evaluation proceeds by scanning the image along the skew angle of the longitudinal construction line. The further analysis proceeds along the logic reflected in the logic diagrams of FIGS. 10-13. Thus, at logic point 55 (FIG. 10) variables are initialized and the program proceeds to scan the sample area pursuant to the previously identified ratio of horizontal to vertical increments in order to scan pixels in a direction parallel to the construction line. At logic point 56 the scan is incremented along the "X" axis. At logic point 57 there is an end of row evaluation. If not end of row, logic proceeds to points 58 and possibly 59, for incrementing the scan either in the "X" direction or the "Y" direction, as indicated. When the proper pixel has been selected, its energy level is evaluated as reflected at logic point 60 (FIG. 11).

Figure 10:
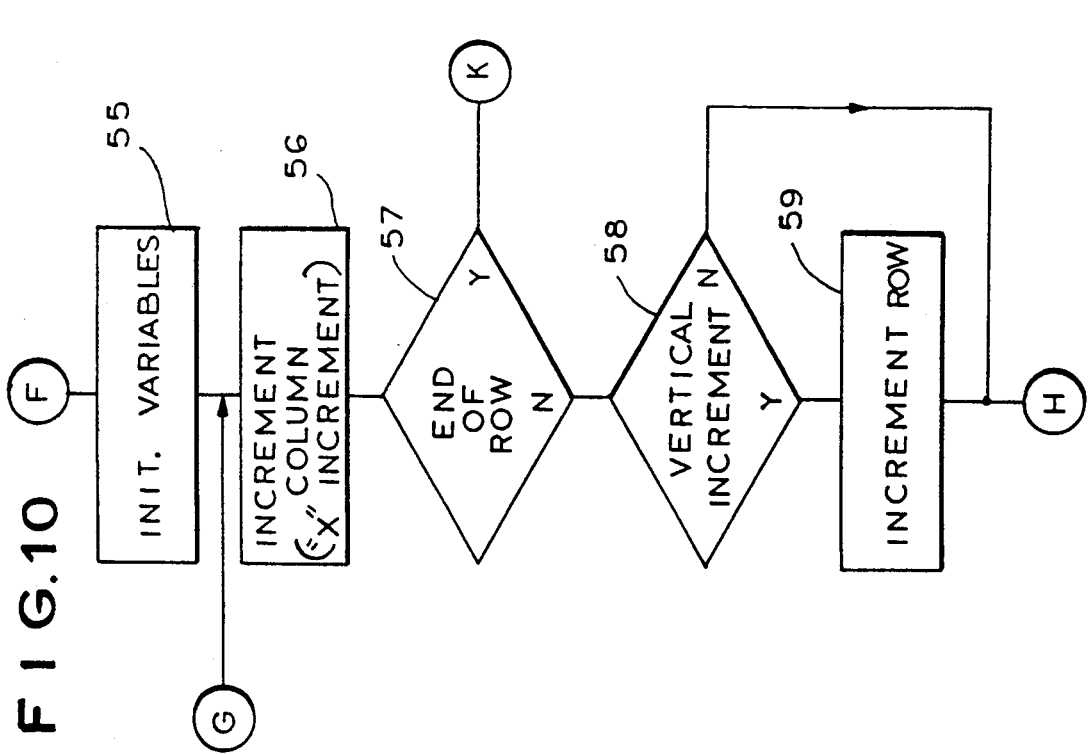
Figure 13:
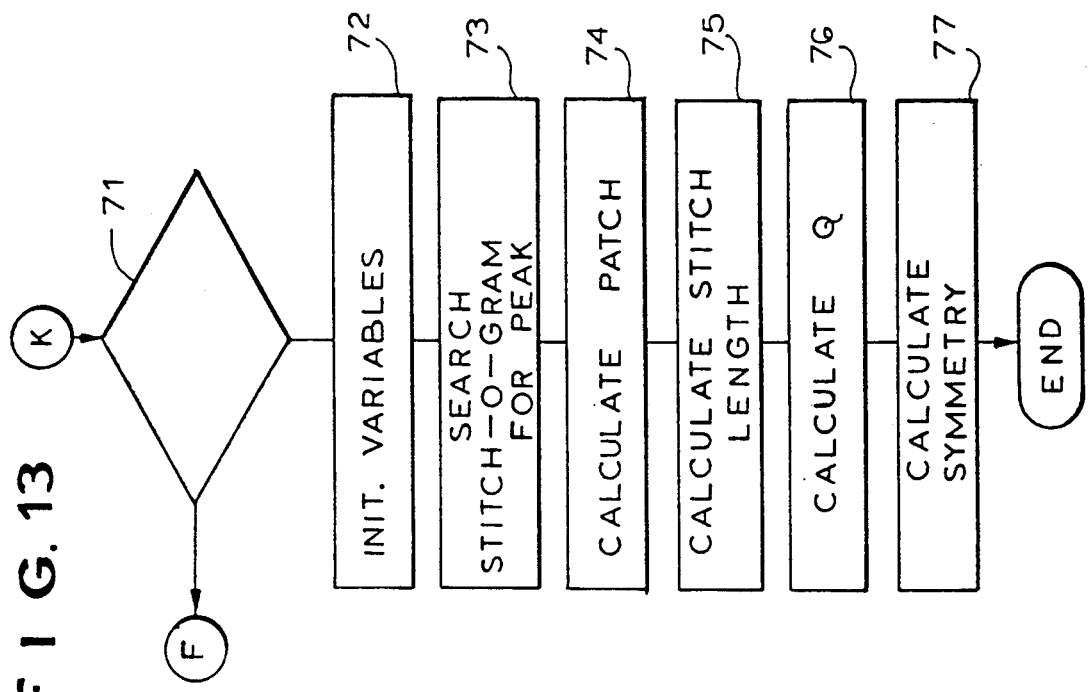
Figure 12:
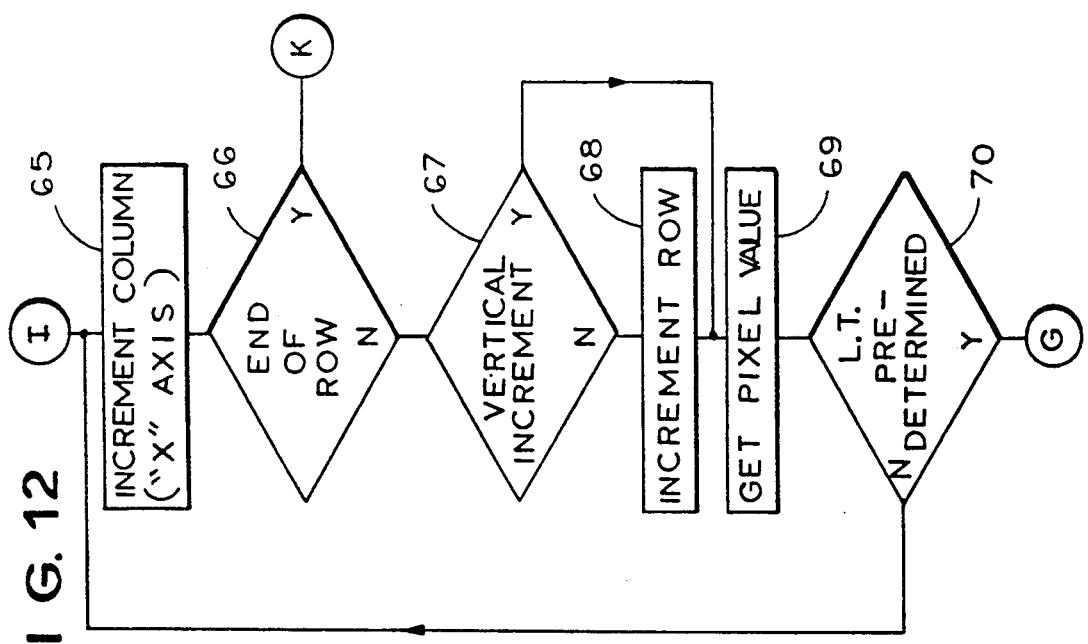

At logic point 61, the energy level of the pixel is evaluated against a threshold energy level representing the presence of an illuminated stitch. If this threshold energy level has not been reached, the program loops back to the logic point 56 (FIG. 10). If the threshold energy level has been exceeded in the pixel being examined, the program proceeds to logic points 62, and/or 63 and/or 64 (FIG. 11). If for a given scanning line, the pixel energy value exceeds the minimum for either the first or second time, logic point 64 is bypassed and the program proceeds to logic points 65-70, shown in FIG. 12. At logic point 65, the scan is incremented along the "X" axis. At logic point 66 a test for end of row is made. If not end of row, the scan is incremented on the "Y" axis, if necessary to follow the construction line, and the next pixel value is read at logic point 69. At logic point 70 a test is made to determine whether the most recent pixel energy value is less than a predetermined value. If not, the program branches back to logic point 65, and a new pixel value along the scan axis is obtained, assuming end of row has not been reached. This cycle continues until a given pixel value is determined at logic point 70 to be less than a predetermined amount, indicating that the scan was at the end of a stitch. At that point, the program branches back to logic point 56 (FIG. 10), where the scan is incremented and a new pixel value is derived, at logic point 60.

The program loops between logic points 56 and 61 until a pixel energy value along the scan axis is indicated to exceed a minimum level, indicating the presence of a stitch. In the case of the first or second stitch reading of the scan line, the program branches directly to logic point 65. The third and subsequent instances, however, cause the program to advance to logic point 64, incrementing a memory-stored value to record a stitch count along the scan axis. The program then proceeds to loop between logic points 66 and 70, as long as the value of each successive pixel along the scan axis exceeds a predetermined amount. When that ceases to be the case, the program returns to logic point 56. The procedures repeat until end of row is indicated at logic point 66, whereupon the program branches to logic point 71 (FIG. 13) where it is examined whether there are more lines to scan on the freeze-frame image. If they are, the program loops back to logic point 55 (FIG. 10) initializing variables, indexing to the next scan line and then proceeding to analyze each pixel along the new scan line for the presence of a stitch, and the subsequent end of that stitch.

After successive scans along each of the scan lines of the freeze-frame image, it is indicated at logic point 71 that all rows have been scanned, and the program proceeds to calculate and display the data of interest. This involves the initialization of variables at logic point 72 scanning the relative memory cells for accumulated stitch count and pixel numbers along each of the scan axis, at logic point 73, calculation and display of the skew angle at logic point 74 and calculation and display of stitches per inch or other linear unit at logic point 75.

For analysis purposes, it may be desirable to calculate and display the standard deviation of stitch count along each of the scanned axis, as well as any lack of symmetry in the distribution of stitch count values. This is suggested at logic points at 76 and 77. These values can be conveniently displayed on a suitable CRT device 80 (FIG. 1) for observation by the machine operator, for example. Abnormalities in the standard deviation and/or symmetry could reflect abnormalities in the fabric for possible malfunction in the system, for example.

In a system according to the invention utilizing a conventional PC/AT system with, for example, a 386, 16 megahertz CPU system, a given freeze-frame image can be processed and evaluated in the manner described within a time frame of approximately 3 seconds. This can easily be reduced to perhaps a second or less by the use of higher speed components and/or additional memory storage capability. For most purposes, however, sampling and evaluation of the fabric at 3 second intervals is quite adequate for realizing extremely close processing control.

It will be readily appreciated that a plurality of imaging units 12 may be employed in connection with a given processing line. For example, separate units, spaced apart in the direction of fabric movement, can be employed to determine the effects of a given processing operation, by evaluating the stitch count and fabric skew both before and after the operation. This is particularly valuable in connection with compressive shrinkage operations, for example. Likewise, a plurality of units may be spaced across the width of the fabric, so that uniformity of stitch count across the width can be evaluated, and conditions such as bowing of the fabric can be readily detected.

A particularly significant feature of the invention is the analysis of the freeze-frame image at the outset, in order to identify and quantify the skew angle of the stitch lines, relative to the direction of longitudinal movement of the fabric. Not only does this avoid an undesirable miscount of the stitches per inch, as a function of measuring stitch lines along an axis angularly offset from the construction lines of the fabric, but it also provides for on-the-fly process control in many cases, in order to correct an undesirable skew condition.

The apparatus employed in the practice of the invention is extremely simple and relatively inexpensive. To considerable advantage, it utilizes an ordinary xenon strobe device in conjunction with a light filter for screening out light in the visible range. The imaging camera thus is responding principally to light in the near infra-red band, between about 830 nanometers and about 1200 nanometers (which is the approximate upper limit of response in the camera), so that the camera is largely insensitive to color variations. This is achieved without, however, resorting to an infra-red strobe device, which could add significant expense to the installation.

It should be understood, of course, that the specific form of the invention herein illustrated and described is intended to be representative only, as certain changes may be made therein without departing from the clear teachings of the disclosure. Accordingly, reference should be made to the following appended claims in determining the full scope of the invention.

We claim:

1. In the process of counting stitches per dimensional unit in a fabric, wherein a digitized freeze-frame image is made of a sample area of the fabric, and an analysis is made of the image to derive a value representative of stitch count, the improvement characterized by
   (a) initially scanning said digitized image in predetermined step-wise sequences of lateral and longitudinal image increments to identify generally linear regions of said image that are substantially uniform in image pattern over an extended length and are thus identifiable as axes extending parallel to lines of construction of said fabric,
   (b) analyzing the ratio of the lateral step-wise increments to the longitudinal step-wise increments to derive a value representative of the skew angle of said lines of construction with respect to the orientation of said image, and
   (c) thereafter scanning successive areas of said digitized image in a pattern of lateral and longitudinal step-wise increments corresponding to said skew angle, whereby to derive a value corresponding to the number of stitches per inch of said fabric in a direction generally parallel with or generally at right angles to said lines of construction.

2. A process according to claim 1, further characterized by,
   (a) said digitized image being scanned in a direction to derive a value representative of the number of stitchs per inch of said fabric in a direction known in relation to said skew angle.

3. A process according to claim 1, further characterized by,
   (a) said digitized freeze-frame image is derived by an imaging camera energized by a strobe flash, and
   (b) the light from said strobe flash is filtered to at least partially eliminate light in the visible wave lengths and thereby render the imaging camera less sensitive to color variations within the sample area of the fabric.

4. A process according to claim 1, further characterized by,
   (a) said imaging camera being energized one or more during the obtaining each freeze-frame image,
   (b) at least the first of such energizations being analyzed to determine the overall level of intensity of imaging light reaching said imaging camera,
   (c) one of said light and said imaging camera being thereafter adjusted as necessary to achieve predetermined levels of image energy, and
   (d) the last of such energizations being utilized to derive said digitized freeze-frame image.

5. A process according to claim 1, further characterized by,
   (a) said digitized image being scanned along a plurality of successive axes, each angularly displaced from the other to ascertain which of the plurality of axes scanned most closely approximates the characteriztics of a construction line of said fabric, and
   (b) thereafter scanning said digitized image with reference to the selected axis, in order to derive stitch count information along axes generally parallel with or generally at right angles to said construction line.

6. In the process of counting stitches per dimensional unit in a fabric, wherein a digitized freeze-frame image is made of a sample area of the fabric, and an analysis is made of the image to derive a value representative of stitch count, the improvement characterized by
   (a) initially scanning said digitized image in predetermined stepwise sequences of lateral and longitudinal image increments along a plurality of angularly displaced axes, in order to identify the lines of construction of said fabric, and
   (b) thereafter scanning successive areas of said digitized image in pattern of lateral and longitudinal step-wise increments corresponding to the orientation of said lines of construction, whereby to derive a value corresponding to the number of stitches per inch of said fabric in a direction generally parallel with or generally at right angles to said lines of construction.

7. A process according to claim 6, further characterized by
   (a) prior to scanning said image, reconstructing the individual pixels of the digitized image by adjusting the gray scale value thereof with reference to the gray scale values of neighboring pixels.

8. A process according to claim 7, further characterized by
   (a) the gray scale values of an individual pixel is adjusted by examining a plurality of pixels in the neighborhood of the individual pixel to determine the lowest gray scale value of the neighboring pixels, and
   (b) reducing the gray scale value of the individual pixel by a value which is a function the lowest gray scale value of said neighboring pixels.

* * * * *